United States Patent [19]
Hoshiko et al.

[11] Patent Number: 4,783,415
[45] Date of Patent: Nov. 8, 1988

[54] GENE CODING FOR SIGNAL PEPTIDES AND UTILIZATION THEREOF

[75] Inventors: Shigeru Hoshiko, Yokohama; Osamu Makabe; Shunzo Fukatsu, both of Tokyo; Kozo Nagaoka, Yokohama, all of Japan

[73] Assignee: Meiji Seika Kabushiki Kaisha, Kyobashi, Japan

[21] Appl. No.: 716,495

[22] Filed: Mar. 27, 1985

[51] Int. Cl.[4] .................. C12N 15/00; C12N 1/20; C12P 21/00; C12P 21/02; C12P 21/04; C12P 19/34; C07H 21/04

[52] U.S. Cl. .................... 435/320; 435/68; 435/70; 435/71; 435/91; 435/172.1; 435/172.3; 435/253; 536/27; 935/9; 935/10; 935/14; 935/29; 935/47; 935/58

[58] Field of Search ............ 435/61, 70, 71, 172.3, 435/91, 172.1, 253, 243, 317, 202, 320; 536/27; 935/14, 9, 10, 47, 48, 72–75

[56] References Cited

U.S. PATENT DOCUMENTS 4,338,400  7/1982  Manis et al. .................. 435/68

FOREIGN PATENT DOCUMENTS 0114695  1/1983  European Pat. Off. ......... 435/172.3
0148552  4/1984  European Pat. Off. ......... 435/172.3
2091268  12/1981 United Kingdom ............. 435/172.3

OTHER PUBLICATIONS

European Search Report–EP 85 30 2177.
Gene, vol. 29, No. 3, Sep. 1984, pp. 315–321, Elsevier Science Publishers, Amsterdam, NL; K. Kendall et al.: "Cloning and Expression of an Extracellular-Agarase Gene from *Streptomyces coelicolor* A3(2) in *Streptomyces lividans* 66".
Nucleic Acids Research, vol. 12, No. 13, Jul. 1984, pp. 5145–5164, IRL Press Ltd., Oxford, GB; M. E. E. Watson: "Compilation of Published Signal Sequences".
Hidaka et al., Chem. Abstr. 95: 20240t (1981).
Palva et al, Proc. Natl. Acad. Sci. USA 79: 5582 (1982).

*Primary Examiner*—James Martinell
*Attorney, Agent, or Firm*—Oblon, Fisher, Spivak, McClelland & Maier

[57] ABSTRACT

A DNA segment of a gene coding for a signal peptide is disclosed the segment is to be used in a host-vector system employing a bacterium belonging to the genus Streptomyces as a host by incorporation in the vector DNA. The segment comprises a DNA having a base sequence coding for the peptide having the amino acid sequence from X to Y in the annexed FIG. 1.

A vector plasmid to be used for transformation of bacteria belonging to the genus Streptomyces is also disclosed. The plasmid comprises a DNA segment with a base sequence coding for an extra-cellular α-amylase derived from *Streptomyces hygroscopicus* SF-1084 strain or a mutant thereof the DNA segment incorporated into a vector plasmid is to be used in a host-vector system employing a bacterium belonging to the genus Streptomyces as a host and also having a DNA segment necessary for expression of the gene information of the DNA segment.

The present invention may be applied to the production of a desired protein which will be secreted outside the host microorganism.

8 Claims, 2 Drawing Sheets

FIG. 1

TGAC<u>GAAGGAG</u>CCACAAG<sup>X</sup>ATGCAGCAACGTTCCCGT
    Z                   MetGlnGlnArgSerArg GTGCTGGGCGGGACGCTCGCCGGAATAGTGGCCGCG
ValLeuGlyGlyThrLeuAlaGlyIleValAlaAla GCGGCGGCCACCGTAGCGCCGTGGCCCTCCCAGGCC<sup>Y</sup>
AlaAlaAlaThrValAlaProTrpProSerGlnAla ACCCCGCCCGGCCAGAAGACCGTCACCGCCACGCTC
ThrProProGlyGlnLysThrValThrAlaThrLeu TTCGAGCGGAAGTACGTCGACGTCGCCAAGGCCTGC
PheGluArgLysTyrValAspValAlaLysAlaTrp ACCGACCAACTGGGCCCGGCCGGCTACGGCTACGTC
ThrAspGlnLeuGlyProAlaGlyTyrGlyTyrVal GAGGTCTCCCCGGCCTC
GluValSerPro

FIG. 2

|—— 1 KILOBASE ——|

StuI      EcoRI
HpaI   AvaI      BamHI   BamHI

GENE CODING FOR SIGNAL PEPTIDES AND UTILIZATION THEREOF

BACKGROUND OF THE INVENTION

1. Field of the Invention

This invention relates to a gene coding for so-called signal peptides. More particularly, the present invention pertains to a DNA fraction of a gene coding for a signal peptide, which is to be used in a host-vector system employing a bacterium belonging to the genus Streptomyces as a host by incorporation in the vector DNA.

2. Background of the Field

By means of bioengineering techniques which have rapidly progressed in recent years, it has become possible to cause hormones such as insulin and growth hormones, vaccines such as that of hepatitis B virus, lymphokines such as interferon and interleukin, and other protein products, all of which had heretofore been produced by higher organisms, to be produced by microorganisms.

Production of such a protein by a geneticaly engineered microorganism is generally practiced according to a process comprising combining a DNA of a gene coding for the amino acid sequence of a desired protein with an implement for introducing into a predetermined microorganism, namely, a vector. The ability to produce the protein is given to the microorganism by introduction of the combined product (generally a plasmid), and culturing the microorganism to produce the protein as a result of the expression of that gene.

More efficient host-vector systems to be used in such a process had been investigated which include, in addition to E. coli, actinomycetes, Bacillus subtilis and yeasts.

Among these hosts, actinomycetes (e.g., bacteria belonging to the genus Streptomyces) are of particular interest. Actinoymcetes are particularly interesting since they can produce β-lactam antibiotics, and moreover the expert in the art is well trained in the handling of these microorganisms especially in relation to safety, through production of antibiotics.

Some actinomycetes excrete protein products outside of the microorganism cells as in the case of extracellular α-amylase Such a phenomenon is speculated to occur by a mechanism in which a gene of the host microorganism, having specific gene information, at once produces a predetermined protein as a precursor containing in addition to the protein sequence a peptide chain which is called a signal peptide. The precursor protein is then secreted through the cell membrane outside the cell or into the periplasmic space, whereby the signal peptide chain is cleaved to produce a mature protein.

This so-called signal hypothesis, although presently widely accepted and based on various experimental facts, has not yet been clarified in regard to what specific amino acid sequence is present in the signal peptide when the host is an actinomycete.

As described above, the biotechnological production of a useful protein by microorganisms is accomplished through the expression of the gene for the protein introduced into the host microorganism via a vector. Accordingly, the incorporation during preparation of the plasmid of a gene coding for a signal peptide into the same plasmid carrying a gene fragment in an actinomycete would give rise to a precursor protein in which the signal peptide is fused with the desired protein, and the desired protein will be secreted outside the host actinomycete by the signal peptide.

SUMMARY OF THE INVENTION

The present invention provides a gene coding for a signal peptide for a host microorganism belonging to the genus Streptomyces.

More specifically, the DNA segment of the gene coding for a signal peptide, which is to be used in a host-vector system employing a bacterium belonging to the genus Streptomyces by incorporation in the vector DNA, comprises a DNA having a base sequence coding for a peptide having the amino acid sequence from X to Y in FIG. 1 annexed hereto.

The vector plasmid for transforming the bacterium of the genus Streptomyces according to the present invention is characterized by carrying a DNA segment comprising a base sequence coding for an extracellular α-amylase derived from Streptomyces hygroscopicus SF-1084 strain or a mutant thereof. The DNA once it is incorporated in a vector plasmid is to be used in a host-vector system employing a bacterium of the genus Streptomyces as a host and also having a DNA sequence necessary for the expression of the gene strand.

When the α-amylase gene of Streptomyces hygroscopicus SF-1084 strain coding for α-amylase as a protein to be produced is excised together with the portion coding for its signal peptide and introduced into an actinomycete for production of the α-amylase by that microoganism via a vector for actinomycetes, most of the α-amylase is found to be secreted outside the microorganism cells.

BRIEF DESCRIPTION OF THE DRAWINGS

FIG. 1 shows a base sequence (from X to Y) of the DNA strand according to the present invention;

FIG. 2 is a restriction endonuclease map of the amylase gene containing the gene coding for the promoter and the signal peptide.

DETAILED DESCRIPTION OF THE INVENTION

Figure 3:
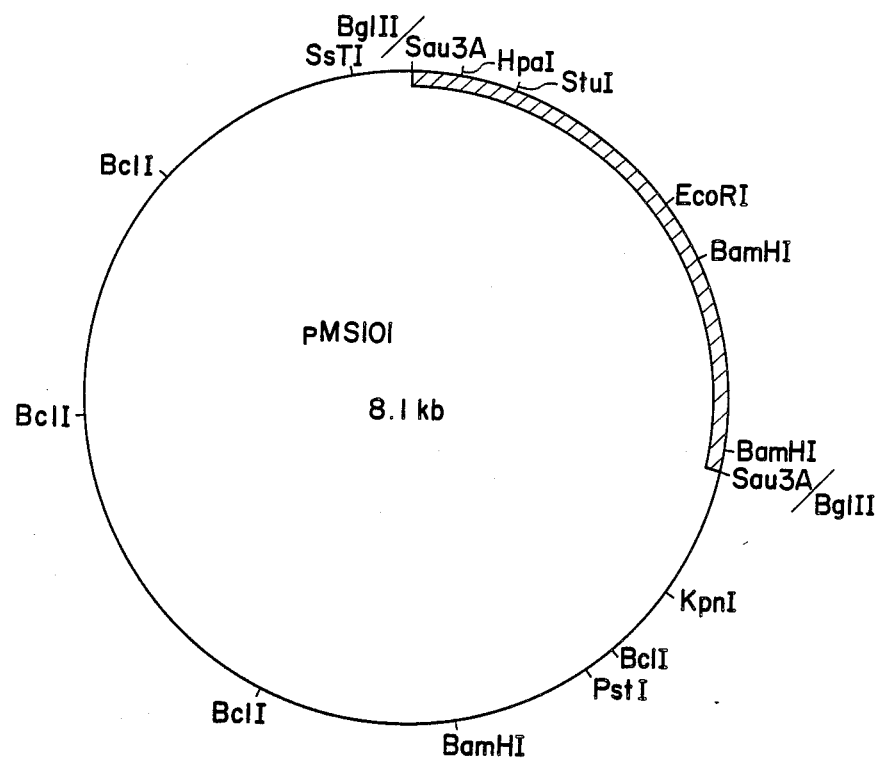
FIG. 3 is a restriction endonuclease cleavage map of the recombinant plasmid pMS 101, the hatched portion indicating the portion containing the amylase gene shown in FIG. 2.

DNA strand coding for the signal peptide

Signal peptide

The DNA segment of the present invention has the base segment coding for the signal peptide this DNA segment is to be used in host-vector system employing as a host a bacterium belonging to the genus Streptomyces by incorporation into a vector DNA.

The signal peptide, which defines the DNA strand of the present invention, has the amino acid sequence of 30 amino acids from X to Y shown in FIG. 1. The amino acid sequence is as follows.

> Met—Gln—Gln—Arg—Ser—
> —Arg—Val—Leu—Gly—Gly—
> —Thr—Leu—Ala—Gly—Ile—
> —Val—Ala—Ala—Ala—Ala—
> —Ala—Thr—Val—Ala—Pro—
> —Trp—Pro—Ser—Gln—Ala

The amino acid sequence was obtained by analysis of the extracellular α-amylase gene of the Streptomyces hygroscopicus SF-1084 strain.

DNA segment of the invention

The gene coding for the signal peptide according to the present invention has a base sequence coding for the peptide with the above amino acid sequence.

Given the amino acid sequence of a peptide, the base sequence coding therefor can easily be determined by reference to a so-called genetic code dictionary.

The DNA segment of the gene coding for the signal peptide according to the present invention has the base sequence from X to Y as shown in FIG. 1 an isomer having a degenerate segment thereof. The "degenerate isomer" as herein mentioned is used to mean different DNA segments coding for the same peptide the "degenerate DNAs have the same base sequence except that degenerate codons are employed. For example, a DNA segment having the same base sequence as that shown in FIG. 1 except that CAG which is the second condon from the 5'-side is replaced with CAA and codes for the same amino acid Gln, is called a degenerate isomer of the DNA strand with the base sequence shown in FIG. 1.

This DNA strand is the gene coding for the signal peptide, and therefore it does not exist solely as the DNA segment with the length of X-Y as shown in FIG. 1. In nature, it exists under a state of association with other DNA segments having various functions linked thereto, e.g. upstream of the 5'-side and (or) downstream of the 3'-side. More specifically, for example, slightly upstream of the 5'-side, the base sequence expected to be the ribosome binding site (represented by Z in FIG. 1) or a DNA fraction constituting the controlling region for promoter or others would exist. The DNA strand of the present invention may also sometimes exist in the form of a plasmid together with the DNA fraction derived from a vector. Accordingly, the DNA strand of the present invention, is said to "comprise a DNA" having the base sequence coding for peptide having a specific amino acid sequence. This language that it is inclusive of such various forms in which the DNA segment exists. In this regard, the nature of the present invention excludes the native state natively in bacteria of the genus Streptomyces from such forms of existence. This is why the DNA strand is defined as "which is to be used by incorporation in the vector".

An example of such a DNA segment of the present invention "comprising DNA" has the base sequence of the structural gene of extracellular (namely, secretory) α-amylase of an actinomycete, namely, the structural gene including the structural gene of the α-amylase itself and the structural gene of the signal peptide regulating extracellular secretion thereof. One example of such an extracellular α-amylase gene is the gene of an extracellular α-amylase derived from *Streptomyces hydroscopicus* SF-1084 strain or a mutant thereof (or one having the same base sequence as that gene).

Another example of such a DNA segment of the present invention "comprising DNA" is that encompassing vector plasmid, as described hereinafter in detail.

Obtaining the DNA segment of the invention

The DNA segment of the present invention has as defined base sequence and therefore it can be prepared according to full chemical synthesis or partial chemical synthesis.

However, since the DNA strand has a considerably long chain length, it may be more convenient to excise it from the gene of an actinomycete.

An example of the method of such an excision from an actinomycete gene comprises excising the α-amylase gene of *Streptomyces hydroscopicus* SF-1084 strain or a mutant thereof together with the portion coding for the signal peptide and thereafter cleaving that portion.

Isolation of such a DNA strand of the desired gene may be performed according to various methods or techniques already known in the field of bioengineering. As to such methods or techniques, reference may be made to the experimental examples as hereinafter described.

Specifically, for example, a DNA segment coding for the signal peptide can be isolated and separated on the basis of the homology of its DNA sequence corresponding to a part of the amino acid sequence of α-amylase or the genetic index of amylase activity.

Utilization of the DNA segment of the invention

The DNA segment according to the present invention is essentially a DNA comprising a gene coding for protein secretion in the signal peptide for an actinomycete. Therefore, if transformation of an actinomycete can be accomplished by a DNA segment, particularly a plasmid, containing signal segment DNA and the DNA segment coding for the desired protein in a state wherein they are capable of replicating and expressing the information on both genes within the actinomycete, it will be possible to obtain the protein produced for secretion to the outside of the cells of the host microorganism.

As the vector to be used for such a method, various kinds of plasmids and phages are known (for example, "Proteins, Nucleic acids, Enzymes", Vol. 260 No. 4, pp, 513–521, published by Kyōritsu Shuppan K.K.). Representative of these are plasmids, which may include typically pIJ702 (Genetics of Industrial Microorganism p. 71, 1982, Kōdansha), pSF689 (FERM BP No. 121, Japanese Patent Laid-Open Publication No. 188600/1982) and pSF765 (FERM BP No. 124, Japanese Patent Laid-Open Publication No. 188600/1982). The above given expression "DNA strand containing . . . in a state wherein they are capable of replicating and expressing both gene informations" means that the vector is capable of being replicated within the intended host (namely an actinomycete), and also that the DNA segment has a promoter or other controlling regions as well as other necessary regions so that the structural gene can be expressed.

As mentioned above, a typical example of the DNA segment of the present invention can be provided in association with a vector plasmid. Thus, the DNA segment of the present invention can be utilized in the form of a vector plasmid for transformation in an actinomycete. The vector may be constructed by incorporating a DNA segment coding for the extracellular α-amylase derived from *Streptomyces hygroscopicus* SF-1084 strain or a mutant thereof cloned in a vector plasmid to be used in the host-vector system employing an actinomycete as a host and also having the DNA necessary for expression of the structural genes possessed by the plasmid.

Methods for the incorporation of a foreign or passenger DNA (e.g., structural genes), such a vector DNA and for transformation with the recombinant plasmid of bacteria of the genus Bacillus are known to those skilled in the art from the teachings in various references as mentioned above or others and the experimental examples set forth below.

EXPERIMENTAL EXAMPLES

An α-amylase producing microorganism *Streptomyces hygroscopicus* SF-1084 strain was inoculated into 80 ml of YMS medium (1% yeast extract, 1% malt extract, 3% soluble starch, and 0.005% triptophan, pH 7.0), and the cells were cultured at 28° C. for 2 days, with shaking, after which the microorganisms were collected by centrifugation at 10,000×g/10 min. From the microorganism cells, the whole DNA was extracted and purified according to the known method of Smith et al. (M. G. Smith: Methods in Enzymology, 12, 545 (1967)) and dialyzed against a TE buffer (10 mM Tris HCl, pH 8.0, 1 mM EDTA) to provide a donor DNA.

The donor DNA thus obtained (10 μg) was digested with 2 units of restriction endonuclease Sau3A in 50 μl of a buffer having a composition of 10 mM Tris HCl, pH 7.2, 10 mM dithiothreitol, and 150 mM NaCl for 10 minutes. After the reaction mixture was shaken with 50 μl of phenol saturated with TE buffer for one minute, the mixture was subjected to centrifugation at 10,000×g/5 min., and the upper layer was isolated by a Pasteur pipette. The aqueous layer containing DNA was extracted twice with ethyl ether and, after removal of phenol, 150 μl of ethanol was added. The mixture was left to stand at −80° C. for 2 hours and then centrifuged at 10,000×g/5 min. to recover the DNA as a precipitate. The DNA recovered was washed once with 500 μl of ethanol, dried under reduced pressure, and then dissolved in 20 μl of pure water sterilized by heating to provide a donor DNA.

Separately, 2 μg of cosmid vector pHC 79 (Barbra Hohn et al.: Gene, 11, 291-298 (1980), commercial product) was digested with 4 units of restriction endonuclease BamHI in a buffer with a composition of 10 mM Tris HCl, pH 7.2, 10 mM dithiothreitol, and 100 mM NaCl at 37° C. for 2 hours. After further heating at 75° C. for 10 minutes, one unit of commercially available alkaline phosphatase derived from *E. coli* was added, and incubation was carried out at 50° C. for one hour. Then, the reaction mixture was treated with phenol, the DNA was precipitated with ethanol, and washed with ethanol, and thereafter the vector DNA was dissolved in 10 μl of sterilized water.

A mixture of 20 μl of the above donor DNA and 10 μl of the above vector DNA was heated at 75° C. for 10 minutes, then cooled gradually to room temperature, and incubated with the addition of 4 μl of a buffer (0.66M Tris HCl, pH 7.6, 66 mM MgCl₂, 0.1M dithiothreitol, 10 mM ATP) and 2 μl if T₄DNA ligase at 22° C. for 14 hours to prepare a recombinant DNA of pHC 79 and *Streptomyces hygroscopicus* DNA.

*E. coli* LE 392 was transformed with this recombinant DNA according to the known method of Horn et al. (Methods in Enzymology, 68, 299-309 (1979). That is, 100 μl of ethanol where added to 36 μl of the recombinant DNA of pHC 79 and *Streptomyces hygroscopicus* DNA, and the mixture was left to stand at −80° C. for 2 hours. This step was followed by centrifugation at 10,000×g/5 min., to recover the recombinant DNA as a precipitate. The precipitate was dissolved in 20 μl of water sterilized by heating, and 10 μl of the solution was added to 50 μl of a solution for forming phage particles in a test tube (commercial product produced according to the method of Horn et al.), which step was followed by incubation at 37° C. for one hour. Then, with the addition of 150 μl of a buffer with a composition of 10 [2 g/μl-DNase I, 10 mM Tris HCl, pH 7.4, 10 mM MgCl₂, 0.1M NaCl, and 0.03% BSA, incubation was conducted at 37° C. for 10 minutes. Then, the solution was centrifuged at 10,000×g/5 min. to recover the supernatant, thereby permitting the recombinant DNA to be taken into the lambda phage particles.

Transduction of the resulting phage particles into *E. coli* K-12 LE392 was done as follows. That is, LE392 was inoculated into 2 ml of L medium containing 0.1% maltose (1% polypeptone, 0.5% yeast extract, and 0.5% NaCl), and, after cultivation overnight, the solution of the lambda phage particles having the recombinant DNA introduced thereinto was added to the culture. Then, each 0.1-ml aliquot of the resultant mixture was applied on a laboratory dish containing L medium comprising 1.5% agar and 50 μg/ml ampicillin, and cultivation was carried out at 37° C. overnight to form a colony, thus permitting LE 392 having the recombinant DNA incorporated therein to appear as a colony.

A recombinant having the amylase gene was selected from this colony according to a known colony hybridization method (Grunstein, M., Hogness, D. S., Proc. Natl. Acad. Sci. U.S.A., 72, 3961-3965 (1975)). The probe employed in this method was a single-stranded synthetic oligonucleotide labelled with $^{32}$P. This oligonucleotide was obtained according to the method described below. That is, this is a mixed probe which consists of at least two kinds of oligonucleotides, and was obtained by synthesis according to the method of M. Caruthers from the oligonucleotides comprising a length of 14 bases estimated from the appropriate 5 continuous amino acid sequence from -X (unknown)-proline-proline-glycine-glutamine-lysine-threonine-valine which is the amino acid sequence on the amino-end side of the amylase protein as determined by Edman degradation (John. E. Shively: Methods in Enzymology, 79, 31-48). The oligonucleotide synthesized was labelled with $^{32}$P by use of γ-$^{32}$P-ATP and T₄polynucleotide kinase, and hybridization was carried out under the conditions of Itakura et al. (Nucleic Acid Research 9, 879-895 (1981)) to select the colony having the desired recombinant gene.

For introduction of the α-amylase gene from pSH1 into the actinomycete *Streptomyces lividans* 66, the known method of Chater et al. [Curr. Topics Microbiol. Immunol., 96, 69 (1981)] was employed. That is, 30 μg of the recombinant DNA pSH1 was digested with 20 units of an endonuclease SstI in 100 μl of a buffer with a composition of 10 mM Tris HCl, pH 7.2, 5 mM MgCl₂ and 75 mM NaCl at 37° C. for 2 hours, and the reaction mixture was subjected to electrophoresis by 0.8% LGT (low melting point) agarose gel/80 mA/3 hours, and the band containing the α-amylase gene was cut out from the gel. The DNA was extracted at 65° C. with phenol and precipitated with ethanol. The DNA containing the α-amylase gene was identified following the known Southern blot technique [Southern, E. M.: J. Mol. Biol., 98, 503 (1975)]; hybridization was carried out at 37° C. with the use of 5×SSC (0.9M NaCl, 0.09M sodium citrate); and the synthetic oligonucleotide labelled with $^{32}$P as previously described was employed as a probe. The DNA fragment containing the α-amylase gene cleaved with SstI and recovered was digested with one unit of an endonuclease Sau3A at 37° for 15 minutes, and the DNA was recovered by phenol extraction-ethanol precipitation and dissolved in 10 μl of water sterilized by heating to obtain a donor DNA.

Separately, after 1 μg of pIJ702, which is a known actinomycete plasmid vector [Journal of General Microbiology, 129, 2703–2714 (1983)], was digested with 2 units of BglII at 37° C. for one hour, 0.5 unit of an alkaline phosphatase derived from E. coli was added, and incubation was carried out at 50° C. for one hour. Then, the DNA was recovered by phenol extraction-ethanol precipitation and dissolved in 10 μl of water sterilized by heating to obtain a vector DNA.

The donor DNA and the vector DNA thus obtained were mixed and incubated with 2 units of T4DNA ligase at 22° C. for 2 hours to prepare a recombinant of pIJ702 with the amylase gene of Streptomyces hygroscopicus.

Streptomyces lividans 66 was transformed with this recombinant as follows. That is, Streptomyces lividans 66 was inoculated into 20 ml of YEME medium (34% sucrose, 0.3% yeast extract, 0.5% bactopeptone, 0.3% malt extract, 1% glucose, 5 mM $MgCl_2$, and 0.5% glycine, pH 7.0), and shaking cultivation was carried out at 32° C. for 36 hours. Mycelia were collected by centrifugation at 10,000×g/10 min., washed once with 10% sucrose solution, and then suspended in 10 ml of P medium (0.3M sucrose, 1.4 mM $K_2SO_4$, 10 mM $MgCl_2$, 0.4 mM $KH_2PO_4$, 25 mM $CaCl_2$, and 25 mM TES buffer, pH 7.2). To the mycelium suspension was added egg white lysozyme with a final concentration of 1 mg/ml, and incubation was conducted at 32° C. for 60 minutes to form protoplasts. The mycelia not converted into protoplasts were removed by cotton filtration. The protoplasts formed were collected by centrifugation at 800×g/7 min. and further suspended in 2 ml of P medium.

A mixture of 100 μl of the protoplast suspension, 100 μl of P-maleic acid buffer with 3/2 concentration (2.5% sucrose, 1.4 mM $K_2SO_4$, 10 mM $CaCl_2$, and 50 mM Tris-Maleic acid buffer, pH 8.0), 50 μl of the recombinant DNA solution, and 375 μl of a polyethylene glycol solution (33% polyethylene glycol #1000/P-maleic acid buffer) was left at room temperature for 60 seconds, diluted with 5 ml of P medium, and centrifuged at 800×g/10 min. to collect protoplasts, which were then suspended in 2 ml of P medium. 0.1 ml of the microorganism suspension was applied on each of 20 laboratory dishes containing R2YE agar medium (0.3 mM sucrose, 1.4 mM $K_2SO_4$, 50 mM $MgCl_2$, 1% glucose, 0.01% Casamino acid, 0.4 mM $KH_2PO_4$, 20 mM $CaCl_2$, 0.3% proline, 25 mM TES buffer, pH 7.2, 5 mM NaOH, 0.5% yeast extract, and 2.2% agar), and after cultivation at 31° C. overnight, a medium comprising 0.8% nutrient broth, 1% Casamino acid, 500 μg/ml tyrosine, 200 μg/ml thiostrepton, 5 μg/ml $CuSO_4 5H_2O$, and 0.5% agar was overlayed thereon. Further, culturing was conducted at 31° C. for 2 days.

As the result, the colony having the recombinant plasmid containing a new DNA fragment at the pIJ702 BglII cleavage site became white, while the colony having pIJ702 itself became black. About 500 of the white colonies were transferred by the replica method into YMS agar medium (1% yeast extract, 1% malt extract, 3% starch, 20 μg/ml thiostrepton, and 1.5% agar, pH 7.2) and NA medium (0.2% nutrient broth, 1% Casamino acid, 500 μg/ml tyrosine, 50 μg/ml thiostrepton, 5 μg/ml $CuSO_4 5H_2O$ and 1.5% agar, pH 7.2), respectively, and cultured at 31° C. for 3 dyas. The bacterial colony grown on YMS medium was treated with $I_2$-KI solution by use of a known method [J. Bacteriol., 119, 416–424 (1974)] to detect those which formed white rings at the periphery of the colony.

From 6 strains among the microorganisms having the recombinant plasmid containing α-amylase gene thus obtained, plasmids were extracted by a known method [J. Bacteriol., 135, 227 (1978)]. One of the plasmids was found to contain a DNA fragment of about 2.4 kilobase (Kb) incorporated therein, and this plasmid was named pMS101. The restriction endonuclease map of 2.3 Kb is shown in FIG. 2, and the restriction endonuclease cleavage map of pMS 101 is shown in FIG. 3.

In order to examine whether or not the α-amylase incorporated in pMS 101 is identical with the α-amylase of Streptomyces hygroscopicus, Streptomyces lividans having pMS101 was inoculated into YMS medium, cultured at 31° C. for 2 days, and the supernatant of the medium was collected by centrifugation. The supernatant (10 μl) was subjected to immunoprecipitation reaction with 10 μL of anti-α-amylase serum obtained from a rabbit previously sensitized with α-amylase derived from Streptomyces hygroscopicus according to the Ouchterlony forming method. As the result, the medium supernatant of Streptomyces lividans 66 having pMS101 and the α-amylase derived from Streptomyces hygroscopicus were found to form uniform precipitation lines, thus indicating that both are identical.

Since the synthetic oligonucleotide corresponding to the amino acid sequence at the amino-end of the α-amylase is hybridized on the DNA fragment sandwiched between HpaI and StuI shown in FIG. 2, the base sequence at this portion was determined by a known method [Methods in Enzymol., 65, 499–560 (1980), ibid. 101, 20–78 (1983)]. A part of the result is shown in FIG. 1. Subsequent to the base sequence portion, which is considered to constitute the signal peptide comprising 30 amino acids from the sequence of ATG which is the protein initiation codon, a base sequence corresponding to the amino acid sequence at the amino-end previously determined was identified. Further, a base sequence of 5'-GAAGGAG-3' (Z in FIG. 1) can be seen upstream of the 5'-side of the protein initiation condon ATG. This is expected to easily form a base pair with a part of the base sequence 3'-UCUUUCCUCCACUAG-5' on the 3'-end side of 16s rRNA of the ribosome constituent of Streptomyces lividans as reported by Bibb et al. [Bibb, M. J., Cohen, S.N., Mol., Gen. Genet., 187, 265 (1982)], and this portion may be expected to become the ribosome binding site. This backs up the fact that the 30 amino acids from methionine to alanine as listed in FIG. 1 constitute the signal sequence for secretion of α-amylase.

Deposition of microorganisms

The microorganisms concerned with the present invention were deposited at Fermentation Research Institute, Agency of Industrial Science & Technology (FERM) as follows.

| Microorganism | Accession No. (FERM BP No.) | Deposition Date |
| --- | --- | --- |
| S. hygroscopicus*[1] SF-1084 | 736 | June 11, 1970 |
| S. lividans 66*[2] | 737 | March 10, 1983 |
| S. lividans 66 (pMS101)*[3] | 740 | February 28, 1984 |
| S. lividans 66 (pIJ0702)*[3] | 739 | " |
| E. coli LE 392*[4] | 738 | " |

-continued

| Microorganism | Accession No. (FERM BP No.) | Deposition Date |
|---|---|---|
| E. coli LE 392 (pSH1)*[3] | 741 | " |

Remarks
*[1]: The bacteriological properties are described in Japanese Patent Publication No. 1871/1974.
*[2]: The bacteriological properties are described in Japanese Patent Application No. 52277/1983.
*[3]: The phenotype or bacteriological properties of these bacteria are not essentially changed from those of the host bacteria except for the change in the genotype introduced by the plasmid or in the genotype due to partial deficiency of the DNA strand from the vector plasmid used which might have occurred during gene recombination in preparation of the plasmid.
*[4]: The bacteriological properties are described in "Molecular Cloning" (ed. by T. Maniatis, Cold Spring Harbor Laboratory).

The plasmids to be suitably used in the present invention are pSF689 and pSF765 as mentioned above, and the microorganisms having these plasmids incorporated therein, namely S. platensis SF-689 and S. fradiae SF-765 are deposited as FERM BP No. 121 and FERM BP No. 124, recpectively.

What is claimed is:

1. A DNA molecule comprising a DNA segment coding for a signal polypeptide having the sequence MetGlnGlnArgSerArg
    ValLeuGlyGlyThrLeuAlaGlyIleValAlaAla
    AlaAlaAlaThrValAlaProTrpProSerGlnAla 2. The DNA molecule of claim 1, wherein the DNA segment has the sequence ATGCAGCAACGTTCCCGT
GTGCTGGGCGGGACGCTCGCCGGAATAGTGGCCGCG
GCGGCGGCCACCGTAGCGCCGTGGCCCTCCCAGGCC 3. The DNA molecule of claim 1 attached to a vector capable of replicating and expressing the signal polypeptide in a Streptomyces bacterium.

4. The DNA molecule of claim 3, wherein the bacterium is Streptomyces hygroscopicus.

5. A composite DNA molecule comprising:
(a) a first DNA segment coding for a signal polypeptide having the sequence MetGlnGlnArgSerArg
    ValLeuGlyGlyThrLeuAlaGlyIleValAlaAla
    AlaAlaAlaThrValAlaProTrpProSerGlnAla (b) a second DNA segment coding for α-amylase; the composite DNA molecule coding for extracellular α-amylase.

6. The composite DNA molecule of claim 5, wherein the second DNA segment coding for α-amylase is obtained from Streptomyces hygroscopicus SF-1084 or a mutant thereof.

7. A composite plasmid comprising:
(a) the DNA segment of claim 5; and
(b) a plasmid vector capable of replicating in a Streptomyces bacterium; said composite plasmid capable of expressing extracellular α-amylase.

8. The composite plasmid of claim 7, capable of expressing α-amylase in Streptomyces hydroscopicus.

* * * * *